(12) United States Patent
Abels et al.

(10) Patent No.: US 6,960,080 B2
(45) Date of Patent: Nov. 1, 2005

(54) ORTHODONTIC BRACKETS WITH ELONGATE FILM HINGE

(76) Inventors: Norbert Abels, Alleestrasse 30a, 66424 Homburg (DE); Claus H. Backes, St. Wendeler Strasse 45, 66113 Saarbrücken (DE)

( * ) Notice: Subject to any disclaimer, the term of this patent is extended or adjusted under 35 U.S.C. 154(b) by 307 days.

(21) Appl. No.: 10/379,331

(22) Filed: Mar. 4, 2003

(65) Prior Publication Data

US 2004/0175667 A1   Sep. 9, 2004

(51) Int. Cl.[7] .............................................. A61C 3/00
(52) U.S. Cl. ............................................ 433/10; 433/11
(58) Field of Search ................................ 433/8–11

(56) References Cited

U.S. PATENT DOCUMENTS

| | | | |
|---|---|---|---|
| 2,011,575 A | 8/1935 | Ford | 433/10 |
| 3,128,552 A | 4/1964 | Broussard | 433/13 |
| 3,218,713 A | 11/1965 | Wallshien | 433/11 |
| 3,724,074 A | 4/1973 | Wallshein | 433/11 |
| 3,748,740 A | 7/1973 | Wildman | 433/11 |
| 3,854,207 A | 12/1974 | Wildman | 433/11 |
| 4,077,126 A | 3/1978 | Pletcher | 433/10 |
| 4,103,423 A | 8/1978 | Kessel | 433/10 |
| 4,144,642 A | 3/1979 | Wallshein | 433/11 |
| 4,171,568 A | 10/1979 | Forster | 433/10 |
| 4,180,912 A | 1/1980 | Kesling | 327/437 |
| 4,279,593 A | 7/1981 | Rohlcke | 433/8 |
| 4,355,975 A * | 10/1982 | Fujita | 433/11 |
| 4,371,337 A | 2/1983 | Pletcher | 433/10 |
| 4,419,078 A | 12/1983 | Pletcher | 433/10 |
| 4,492,573 A | 1/1985 | Hanson | 433/11 |
| 4,512,740 A | 4/1985 | Kurz | 433/22 |
| 4,527,975 A | 7/1985 | Ghafari et al. | 433/8 |
| 4,559,012 A | 12/1985 | Pletcher | 433/10 |
| 4,559,013 A | 12/1985 | Amstutz et al. | 433/22 |
| 4,597,739 A | 7/1986 | Rosenberg | 433/16 |
| 4,614,497 A | 9/1986 | Kurz | 433/8 |
| 4,634,662 A | 1/1987 | Rosenberg | 433/10 |
| 4,655,708 A | 4/1987 | Fujita | 433/10 |
| 4,687,441 A | 8/1987 | Klepacki | 433/8 |
| 4,698,017 A | 10/1987 | Hanson | 433/11 |
| 4,712,999 A | 12/1987 | Rosenberg | 433/8 |
| 4,786,252 A | 11/1988 | Fujita | 433/10 |
| 4,846,681 A | 7/1989 | Mourany et al. | 433/11 |
| 4,850,865 A | 7/1989 | Napolitano | 433/8 |

(Continued)

FOREIGN PATENT DOCUMENTS

DE   1 184 451   12/1964

(Continued)

OTHER PUBLICATIONS

Konstruieren mit Kunststoffen, Gunter Erhard, Carl Hanser Verlag Munchen Wien, pp. 314-329, 1999.

*Primary Examiner*—John J Wilson

(57) ABSTRACT

An orthodontic bracket comprises a bracket base, an arch wire slot configured to receive an arch wire, a ligation cover, an elongate film hinge that interconnects the bracket base and ligation cover, and a cam structure. The ligation cover is selectively rotatable about the film hinge relative to the bracket base between an open, non-ligating position and closed, ligating position relative to the arch wire slot. The cam structure includes a curved surface proximal to the elongate film hinge that assists in distributing forces throughout the entire length of the film hinge as the cover is rotated relative to the bracket base. The cam structure also includes a camming surface that biases the ligation cover toward the open, non-ligating position. The ligation cover covers at least a portion of the slot when in the closed, ligating position.

23 Claims, 5 Drawing Sheets

U.S. PATENT DOCUMENTS

| | | | |
|---|---|---|---|
| 4,859,179 A | 8/1989 | Kesling | 433/8 |
| 5,037,296 A | 8/1991 | Karwoski | 433/8 |
| 5,062,794 A | 11/1991 | Miura | 433/10 |
| 5,078,596 A | 1/1992 | Carberry et al. | 433/8 |
| 5,094,614 A | 3/1992 | Wildman | 433/14 |
| 5,125,832 A | 6/1992 | Kesling | 433/8 |
| 5,160,260 A | 11/1992 | Chang | 433/8 |
| 5,161,969 A | 11/1992 | Pospisil et al. | 433/8 |
| 5,174,754 A | 12/1992 | Meritt | 433/8 |
| 5,224,858 A | 7/1993 | Hanson | 433/10 |
| 5,275,557 A | 1/1994 | Damon | 433/10 |
| 5,322,435 A | 6/1994 | Pletcher | 433/11 |
| 5,344,315 A | 9/1994 | Hanson | 433/20 |
| 5,356,288 A | 10/1994 | Cohen | 433/8 |
| 5,380,197 A | 1/1995 | Hanson | 433/22 |
| 5,429,499 A | 7/1995 | Sernetz | 433/8 |
| 5,456,599 A | 10/1995 | Hanson | 433/8 |
| 5,470,228 A | 11/1995 | Franseen et al. | 433/8 |
| 5,474,445 A | 12/1995 | Voudouris | 433/10 |
| 5,474,446 A | 12/1995 | Wildman et al. | 433/14 |
| 5,556,276 A | 9/1996 | Roman et al. | 433/8 |
| 5,562,444 A | 10/1996 | Heiser et al. | 433/11 |
| 5,586,882 A | 12/1996 | Hanson | 433/13 |
| 5,630,715 A | 5/1997 | Voudouris | 433/8 |
| 5,630,716 A | 5/1997 | Hanson | 433/14 |
| 5,685,711 A | 11/1997 | Hanson | 433/11 |
| 5,711,666 A | 1/1998 | Hanson | 433/11 |
| 5,738,513 A | 4/1998 | Hermann | 433/13 |
| 5,857,849 A | 1/1999 | Kurz | 433/10 |
| 5,863,199 A | 1/1999 | Wildman | 433/10 |
| 5,885,074 A | 3/1999 | Hanson | 433/13 |
| 5,906,486 A | 5/1999 | Hanson | 433/11 |
| D412,363 S | 7/1999 | Stevens | D24/180 |
| D412,579 S | 8/1999 | Stevens | D24/180 |
| D412,988 S | 8/1999 | Stevens | D24/180 |
| 5,938,435 A | 8/1999 | Raspino, Jr. | 433/2 |
| 5,964,589 A | 10/1999 | Musich | 433/20 |
| 6,017,118 A | 1/2000 | Gasvoda et al. | 347/86 |
| 6,042,373 A | 3/2000 | Hermann | 433/13 |
| 6,042,374 A | 3/2000 | Farzin-Nia et al. | 433/13 |
| 6,071,119 A | 6/2000 | Christoff et al. | 433/14 |

FOREIGN PATENT DOCUMENTS

| | | | |
|---|---|---|---|
| DE | 23 57 573 | 5/1975 | |
| DE | 91 12 872.2 | 3/1992 | |
| DE | 296 08 349 U1 | 7/1996 | |
| EP | 0 714 639 A2 | 5/1996 | |
| EP | 0 714 639 A3 | 5/1996 | |
| WO | WO 94/00072 | 6/1994 | |
| WO | WO 00/33760 | 6/2000 | A61C 7/28 |
| WO | WO 00/76419 | 12/2000 | |

* cited by examiner

ORTHODONTIC BRACKETS WITH ELONGATE FILM HINGE

BACKGROUND OF THE INVENTION

1. The Field of the Invention

The present invention relates to orthodontic brackets, more particularly to self-ligating orthodontic brackets that include a base, at least one slot for receiving an arch wire, a ligating cover, and a flexible film hinge.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct underbites or overbites. For example, orthodontic treatment can improve the patient's occlusion, or enhanced spatial matching of corresponding teeth.

The most common form of orthodontic treatment involves the use of orthodontic brackets and wires, which together are commonly referred to as "braces". Orthodontic brackets, more particularly the orthodontic bases, are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment. End sections of the arch wire are typically captured within tiny appliances known as "buccal tubes" affixed to the patient's molars.

There are two distinct classes of orthodontic brackets: those that require the use of ligatures to fasten the arch wire to the bracket, and those that are self-ligating. In brackets of the first class, small ligature wires are typically used to hold the arch wire in a securely seated position in the brackets. Ligatures or some other form of fastening means are essential to ensure that the tensioned arch wire is properly positioned around the dental arch, and to prevent the wire from being dislodged from the bracket slots during chewing of food, brushing of teeth, or application of other forces. One type of commercially available ligature is a small, elastomeric O-ring, which is installed by stretching the O-ring around small wings known as "tie wings" that are connected to the bracket body. Metal ligatures are also used to retain arch wires within the bracket slots.

In an effort to simplify the process of installing braces, a variety of self-ligating brackets have been developed. The term "self-ligating bracket" refers to a class of orthodontic brackets that include some sort of cover, whether separate from or hingedly or slidably attached to the base, which encloses or otherwise retains the arch wire within the slot of the base.

Self-ligating brackets have grown in popularity because of their convenient features, but they still exhibit certain disadvantages. Often, special tools are required in order to either open or close existing self-ligating brackets, they must be assembled from extremely small parts, they may require special machining steps, and they can be rather fragile. Examples of self-ligating brackets are disclosed in U.S. Pat. Nos. 3,748,740, 4,077,126, 5,857,849, and 6,071,118. In general, existing self-ligating brackets are complicated in design, complex to assemble, and difficult to use in practice. They often require many trips to the orthodontist for periodic readjustment and maintenance.

Therefore, there exists a need for new designs and materials that can simplify the installation and subsequent maintenance of orthodontic brackets. In particular, there is a need for orthodontic brackets that are easy to open and close, that do not require complicated tools for their use, that can be easily and inexpensively manufactured and installed by the orthodontist, and that provide greater versatility together with a simplified design while at the same time exhibiting strength and durability.

BRIEF SUMMARY OF THE INVENTION

Generally, the orthodontic brackets of the present invention include a bracket base, a ligating cover, an arch wire slot for receiving an arch wire, an elongate film hinge, and a curved or camming structure that interacts with at least one of the film hinge and bracket base. The orthodontic brackets according to the present invention are generally low-cost, simple to manufacture, compact in construction, and incorporate one or more of the inventive features and improvements disclosed herein.

The orthodontic bracket is preferably formed as one single piece, requiring no assembly. This reduces the cost and complexity of manufacture and prevents unwanted separation of the bracket parts. In a preferred embodiment, the inventive orthodontic bracket can be made from a single type of material, e.g., plastic. Although other methods may be used, low cost manufacture is possible by forming the bracket by injection molding.

The brackets of the present invention are self-ligating, i.e., the arch wire is clamped or otherwise held between the ligation cover and the bracket base. The ligating cover is attached to the base by the elongate film hinge, and the cover is rotatable about the film hinge relative to the bracket base between an open, non-ligating position relative to the arch wire slot and a closed, ligating position relative to the arch wire slot. A curved structure may operate in conjunction with the film hinge to improve the functionality of the bracket. In addition to or instead of the curved structure, a camming structure may be provided that biases the ligation cover toward the open, non-ligating position.

The elongate film hinge is characterized by its ability to distribute forces and stresses associated with operation of the hinge along substantially its entire length. This is in contrast to other types of film hinges where the forces and stresses are concentrated at one point or line, which can create a localized area where the film hinge is more radically stressed and can more easily break. Because the elongate film hinge can be bent over its entire length, it can be made of a thicker, more durable construction while still providing adequate bendability, flexation and resilience. In general, the hinge is sufficiently thick so as to provide adequate strength, but sufficiently thin so as to provide adequate flexibility, bendability and resilience. The result is an improved film hinge that can resist breakage when exposed to shearing and bending forces, such as may occur during placement and use of the orthodontic brackets.

Operation of the orthodontic bracket may be enhanced by a cam structure that is attached to an inner surface of the ligation cover and that extends toward the bracket base. The cam structure can be configured to provide at least one or both of the following: (1) a camming surface that interacts with the base so as to bias the cover toward an open, non-ligating position relative to the arch wire slot of the bracket base; and (2) providing a curved surface that helps ensure that the elongate film hinge bends gradually over substantially its entire length rather than abruptly at any specific location. In this way, mechanical forces can be distributed over substantially the entire length of the film hinge, thereby reducing the tendency of the film hinge to become fatigued and fractured during normal use.

When the ligation cover is in the closed, ligating position, the cam structure is preferably received within a recess that exists between the base and the film hinge. This results in a uniform and continuous smooth surface on the outside of the bracket, resulting in increased comfort and safety. It also helps keep food or other contaminants from becoming lodged in the bracket (e.g., within the space that would otherwise exist between the bracket base and film hinge).

The bracket of the present invention is self-ligating, i.e. the arch wire is clamped between the cover and the base. The ligation cover may advantageously include a latch member that interacts with a corresponding recess of the bracket base in order to selectively lock and unlock the cover relative to the base.

In addition, the cover may optionally include a bearing protrusion that aligns with or extends partially into the arch wire slot so as to provide force when the cover is closed in a manner so that the bearing protrusion fixes the arch wire. Alternatively, the cover may optionally include a spring or spring-like feature that provides continuous force onto the arch wire as the arch wire becomes better seated within the arch wire slot during the desired tooth-straightening process.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

The orthodontic brackets of the present invention include a base, a ligating cover, an arch wire slot for receiving an arch wire, an elongate film hinge, and at least one curved or camming structure. The bracket may optionally be formed as one single piece, requiring no assembly. This reduces the cost and complexity of manufacture and prevents unwanted separation of the bracket parts.

In a preferred embodiment, the inventive orthodontic bracket can be made (e.g., by injection molding) from a single type of material, e.g., plastic. The smooth, non-stick nature of plastic as compared to metal or other materials traditionally used in bracket construction improves the ability to efficiently straighten teeth with less required adjustment because the use of plastic as opposed to metal or other material reduces unwanted or unnecessary friction between the arch wire and the bracket associated with desired movement of the teeth. Attention is now turned to the drawings, which illustrate exemplary embodiments of orthodontic brackets according to the invention.

Figure 1:
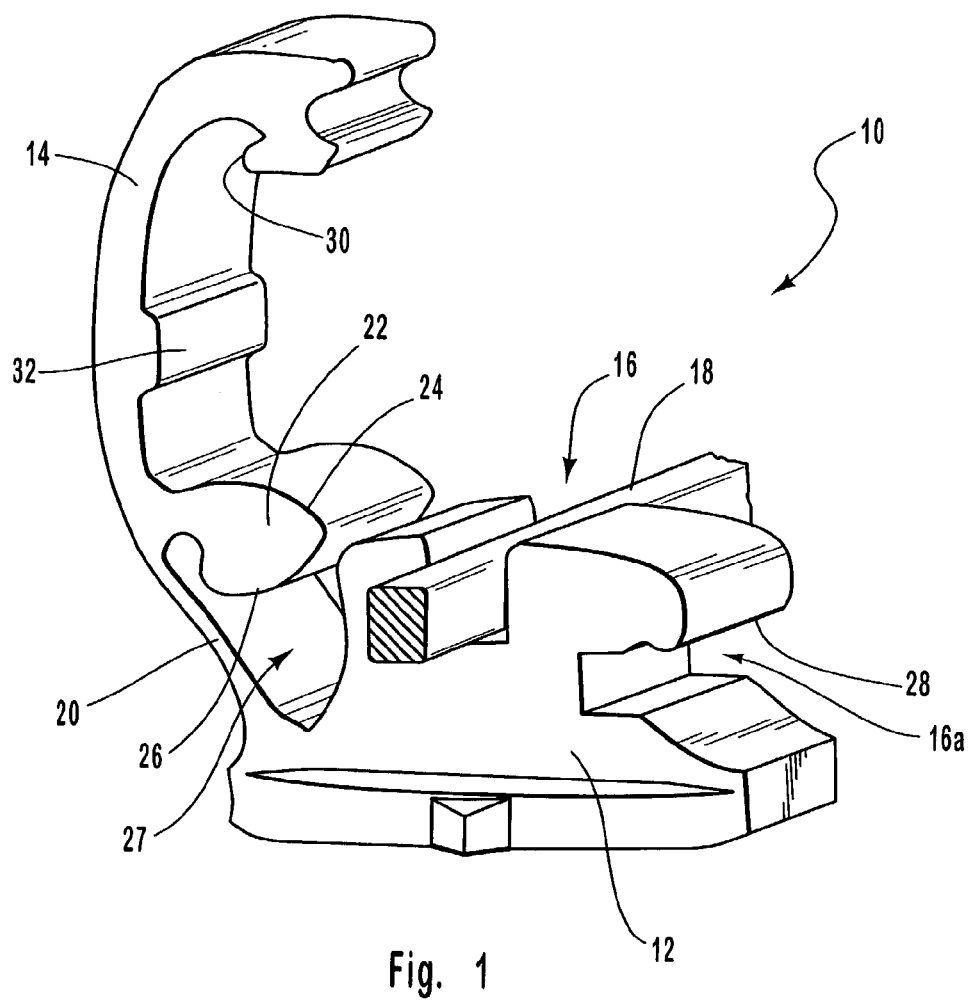
FIG. 1 is a perspective view of an exemplary orthodontic bracket according to the invention in which the ligation cover is in an open, non-ligating position.
Figure 2:
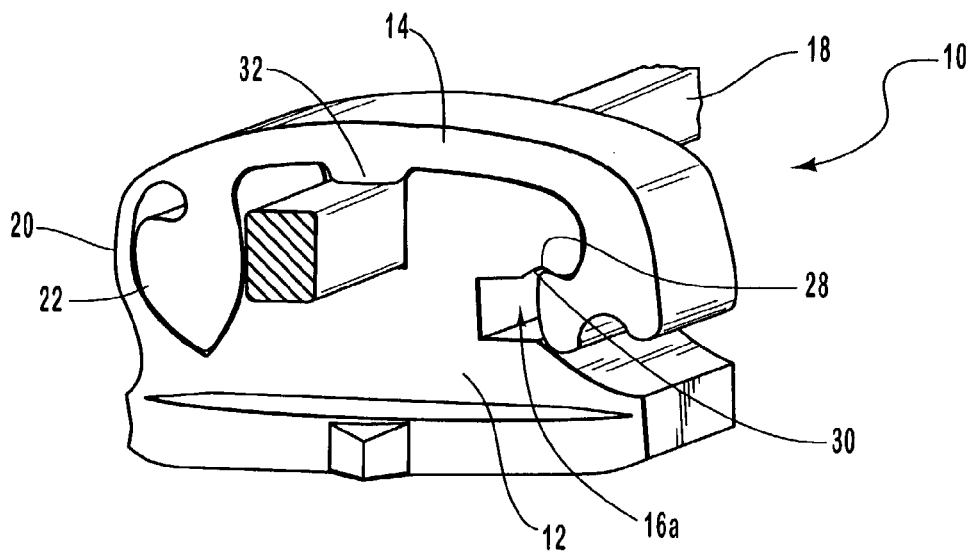
FIG. 2 is a perspective view of the bracket shown in FIG. 1 in which the ligation cover is in a closed, ligating position.

FIGS. 1 and 2 depict an orthodontic bracket 10 having a bracket base 12 to which a ligation cover 14 is hingedly attached. An arch wire slot 16 open to the upper side of the bracket base 12 is provided near the center of the base 12 and serves for the receipt of an arch wire 18 therein. The arch wire 18, shown with a square cross-section (any other cross section known in the art could be used), is arranged inside the arch wire slot 16 and assists in providing the necessary forces to correct the teeth in a known manner. As illustrated in FIGS. 1 and 2, the orthodontic bracket 10 may include an additional arch wire slot 16a. Ligation of an additional or alternate arch wire (not shown) may be accomplished in the same way as ligation of an arch wire in slot 16, i.e., by closing the ligation cover 14 over the bracket base 12.

The orthodontic bracket 10 further includes an elongate film hinge 20 that is attached at one end to the bracket base 12 and at an opposite end to the ligation cover 14. In this way, the ligation cover 14 is hingedly attached to the bracket base 14 and is able to be selectively rotated between an open, non-ligating position and a closed, ligating position relative to the bracket base 12, more particularly the arch wire slot 16. The ligation cover covers or occludes at least a portion of the arch wire slot 16 when in the closed, ligating position. The elongate film hinge 20 is a variation and improvement of the integral film hinge of the inventors that was first disclosed in U.S. application Ser. No. 09/784,525, filed Feb. 15, 2001.

Because the film hinge of orthodontic brackets of the invention are elongated, they are able to bend gradually over their entire length rather than at a single point or line. This results in a hinge that is more resilient and durable over time because it is not overly bent or stressed at any particular point or line along its length. Moreover, because the elongated film hinge can bend gradually over substantially its entire length, it can be of a thicker, stronger construction compared to a film hinge that bends at a single point or line. This results in a hinge that is significantly stronger and more resistant to breakage compared to previous embodiments of the film hinge. In order to maximize strength while providing sufficient bendability, the elongated film hinges according to the invention are advantageously formed as thick as possible to provide maximum strength while being sufficiently thin to allow the hinge to bend with sufficient flexibility and resilience when in use. In general, the elongate film hinges according to the invention preferably have a thickness in a range of about 0.1 mm to about 0.4 mm, more preferably in a range of about 0.15 mm to about 0.3 mm, and most preferably in a range of about 0.2 mm to about 0.26 mm.

In some embodiments, the elongate film hinge will have a cross-sectional thickness that is less than the cross-sectional thicknesses of the adjoining ligation cover and bracket base. Nevertheless, it is within the scope of the invention for the elongate film hinge to have a material cross section that is as thick or thicker than the adjoining ligation cover and/or bracket base.

Preferably, the orthodontic bracket also includes a curved surface that interacts with the elongate film hinge to assist in causing the hinge to bend gradually along substantially its entire length as the ligation cover is selectively rotated relative to the bracket base. This curved surface may either comprise an integral part of the ligation cover or bracket base, or alternatively, a separate piece attached to the cover or bracket base. In one embodiment, the curved surface may be part of a cam structure that is integrally attached to the ligation cover, as illustrated in FIG. 1.

In FIG. 1, a cam structure 22 is illustrated that has a camming surface 24 and a curved hinge-guiding surface 26. The hinge-guiding surface 26 is an example of a curved surface that interacts with the elongate film hinge 20 to assist in gradually bending the film hinge along substantially its entire length as the ligation cover is rotated relative to the bracket base. The hinge-guiding surface 26 is advantageously curved so as to interact with the elongate film hinge 20 by distributing forces along substantially its entire length as the ligation cover 14 is rotated. Distributing forces along the length of the elongate film hinge 20, rather than allowing the forces to concentrate at a single location, results in a hinged bracket that is more resistant to breakage of the film hinge compared to brackets in which the film hinge is bent abruptly at a specific point or line. In one embodiment, the hinge-guiding surface 26 may help maintain the ligation cover 14 (in combination an exemplary latch mechanism discussed more fully below) in the locked position by exerting outward pressure against the elongate film hinge 20. This, in turn, effectively shortens length of the ligation cover 14, thereby causing the exemplary latch mechanism to hold the ligation cover 14 more tightly.

The camming surface 24 is curved or angled in such a way so that it interacts with the bracket base 12 in order to bias the ligation cover 14 toward the open, non-ligating position when the cover is in an unlocked configuration relative to the bracket base 12. This improves access to the arch wire slot 16, making insertion or removal of an arch wire easier.

In the embodiment illustrated in FIG. 1, cam structure 22 is integrally attached to the inner surface of the ligation cover 14 in a manner so as to extend toward the bracket base 12. Further, and as is shown in particular in FIG. 2, the cam structure 22 is received within a recess 27 between the bracket base 12 and the elongate film hinge 20 when the ligation cover 14 is in the closed position. This results in a uniform smooth continuous surface along the top of the bracket 10. A uniform smooth and continuous surface results in greater safety and comfort for the patient, while also keeping food particles or other contaminants from becoming lodged in the bracket. The cam structure 22 also occupies the space 27 in order to displace debris that might otherwise lodge there.

The orthodontic brackets according to the invention may advantageously include a locking system for maintaining the ligation cover 14 in a closed, ligating position once the cover has been closed relative to the bracket base. The illustrated embodiment shows an exemplary latch mechanism in which increased pressure by an arch wire bearing upwardly against the ligation cover 14 results in tighter locking of the cover 14 to the bracket base 12. In the illustrated embodiment, an angled keyway 28 is provided near one end of the bracket base 12. The ligation cover 14 contains a corresponding locking tongue 30 that is insertable within the angled keyway 28. Alternative latch mechanisms, such as those disclosed in U.S. application Ser. No. 09/953,400, filed Sep. 12, 2001, may alternatively be used. Operation of the exemplary locking system will be explained in further detail below when discussing FIGS. 3A–3E.

A bearing protrusion 32 may be provided on the inside and middle of the ligation cover 14 that extends toward the arch wire slot 16 when the ligation cover 14 is in the closed position. The bearing protrusion 32 assists in fixing the arch wire 18 within the arch wire slot 16 when the ligation cover is in the closed state (FIG. 2). The bearing protrusion 32 helps to maintain proper pressure by the ligation cover 14 onto the arch wire 18, particularly when the arch wire 18 is completely seated within the arch wire slot 16.

Figure 3A:
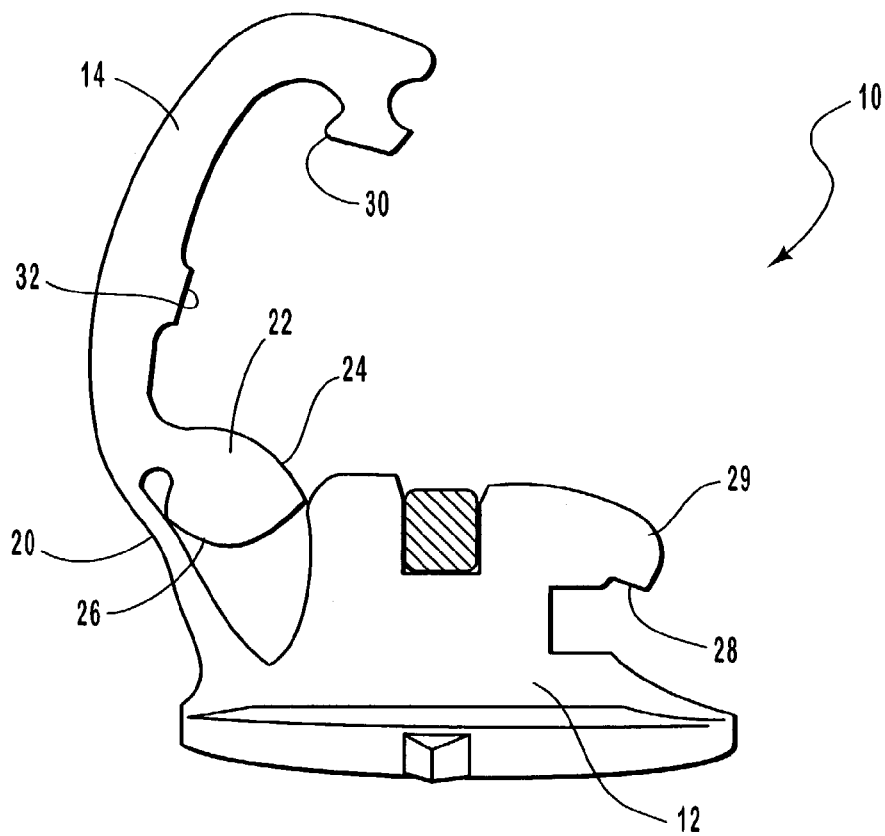
FIGS. 3A–3E illustrate operation of the bracket shown in FIG. 1 as the ligation cover is moved from the open, non-ligating position to the closed, ligating position.
Figure 3B:
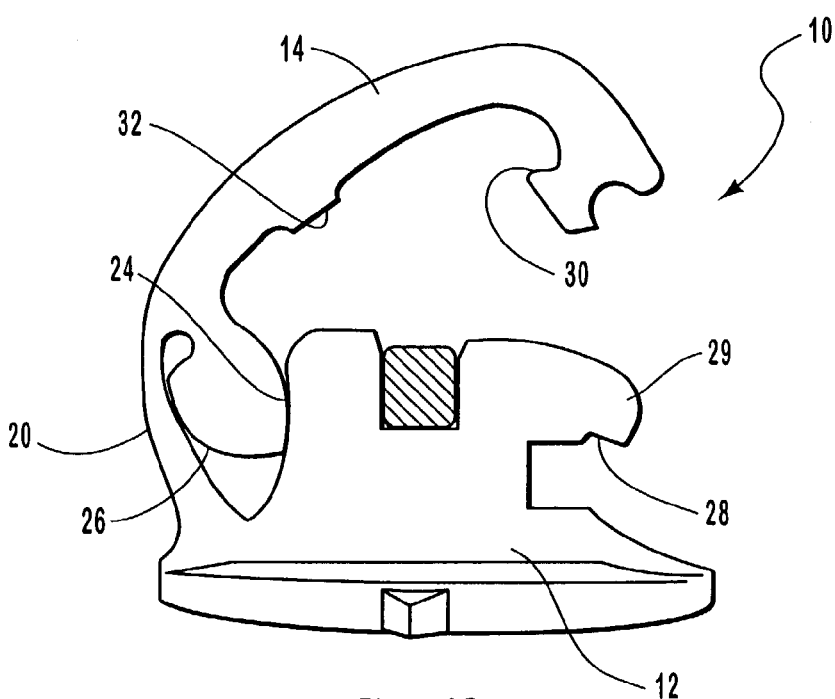
Figure 3C:
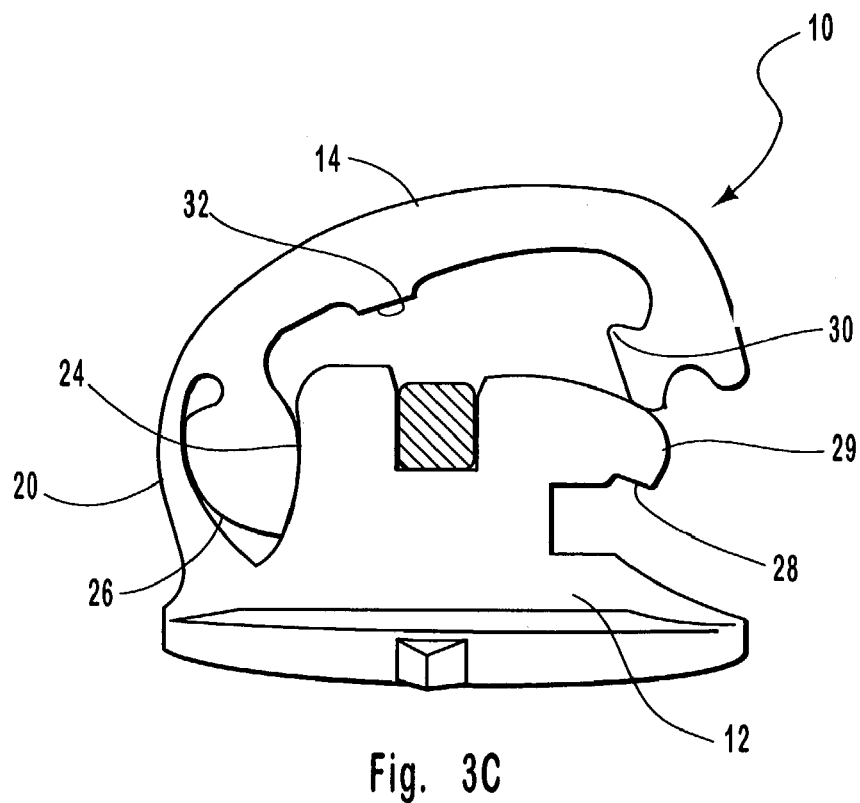
Figure 3D:
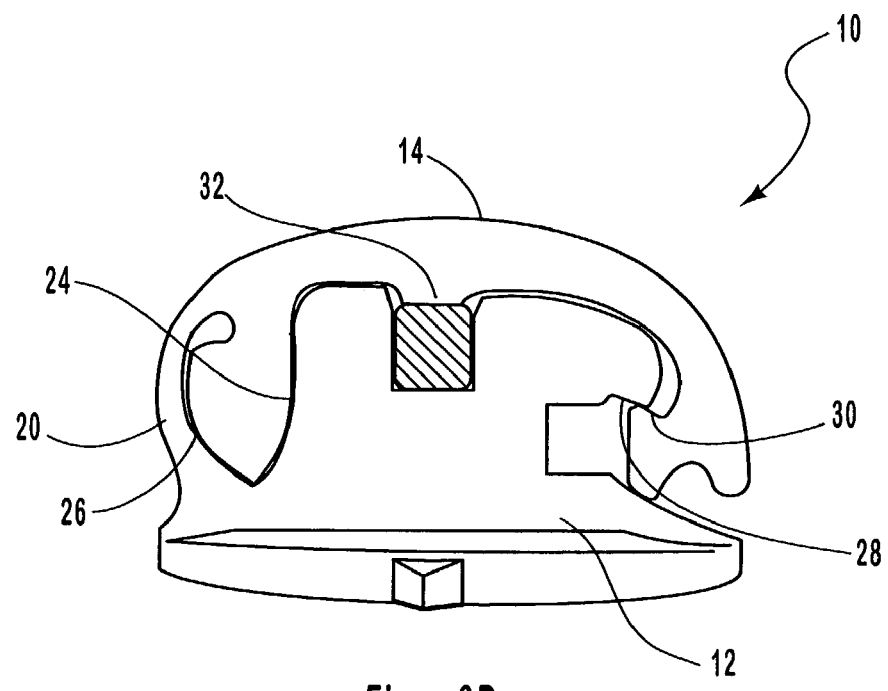
Figure 3E:
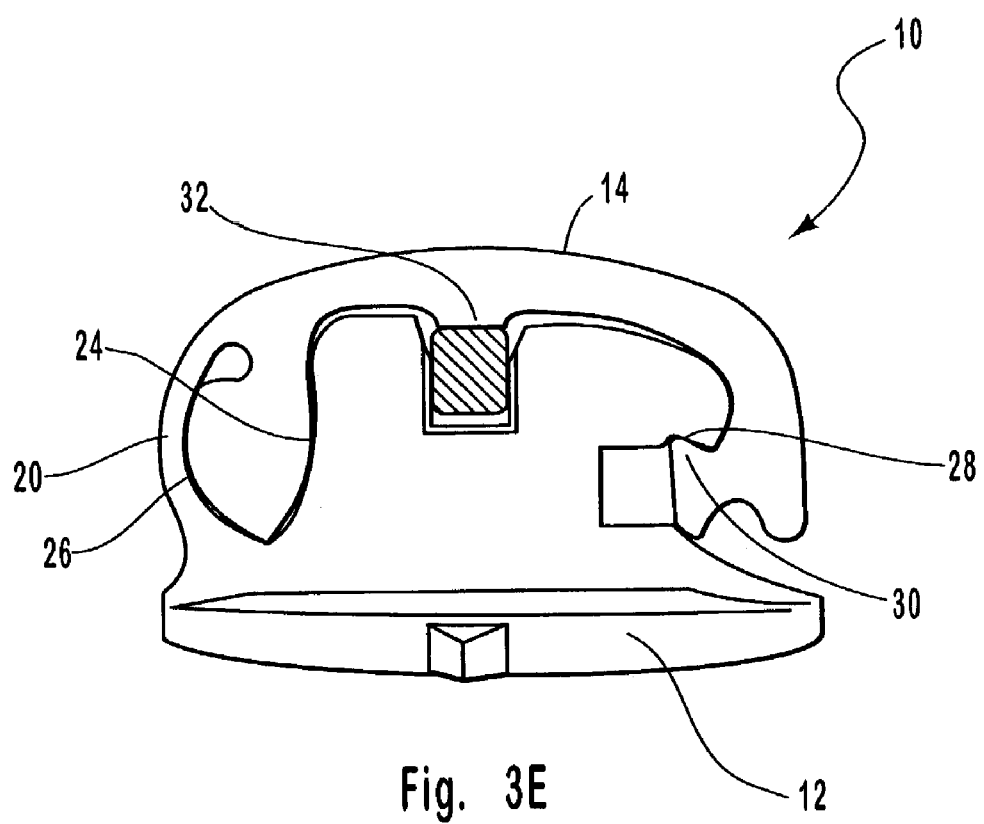

FIGS. 3A–3E are provided in order to better describe and illustrate the operation of the orthodontic bracket 10 as the ligation cover 14 is moved from an open position (as seen in FIG. 3A) to a closed position (as seen in FIG. 3E).

FIG. 3A is a side view that shows the orthodontic bracket 10 with the ligation cover 14 in an open position relative to the bracket base 12, more significantly in a non-ligating position relative to the arch wire slot 16. The ligation cover 14 can be manually opened by rotating it about the elongate film hinge 20 so that the cam structure 22 just barely abuts an upper surface of the bracket base 12. It will be appreciated, however, that, depending on the nature of the elongate film hinge 20, it is possible for the ligation cover 14 to be biased either toward or away from the bracket base 12 when the ligation cover 14 is in a fully open position relative to the bracket base 12. In the embodiment shown in FIG. 3A, however, the elongate film hinge 20 gently biases the ligation cover 14 toward the bracket base 12 in order for the cam structure 22 to lightly contact an upper surface of the bracket base 12.

As seen in FIG. 3B, when the ligation cover 14 is pushed down toward the bracket base 12, the camming surface 24 of the cam structure 22 makes abutting contact with, and slides against, an upper surface of the bracket base 12, thereby causing the cam structure 22 to be biased in a spring-like fashion towards the elongate film hinge 20. As a result, the cam structure 22 can act as a spring that exerts an opposing biasing force that, in combination with the camming action or camming surface 24, biases or urges the ligation cover 14 toward the open, non-ligating position relative to the bracket base 12. Thus, if the bracket 10 is in the conformation depicted in FIG. 3B and the ligation cover 14 is released, it may spontaneously spring back to a conformation like the one illustrated in FIG. 3A. It should be understood, however, that the exact resting conformation of the ligation cover 14 is dependent upon the size, shape and relative positions of the cam structure 22 and the upper surface of the bracket base 12 with which it comes into contact.

As the ligation cover 14 is pushed down further toward the bracket base 12 as seen in FIG. 3C, the camming surface 24 of the cam structure 22 continues to make contact with the bracket base 12, thus pushing the cam structure 22 further toward the elongate film hinge 20. Thus, if the bracket 10 is in the conformation depicted in FIG. 3C, and the ligation cover 14 is released, it will spontaneously spring back to a conformation like the one illustrated in FIG. 3A (subject to the actual size, shape and angles of the cam structure 22 and bracket base 12). This tendency of the ligation cover 14 to remain in an open, non-ligating position absent external force is advantageous to the dental practitioner because it facilitates the insertion of an arch wire into the arch wire slot. It is easier for a dental practitioner to insert an arch wire into the arch wire slot 16 when using a bracket that spontaneously opens to a non-ligating position, as opposed to a bracket in which the ligation cover is continuously biased so as to cover or occlude the arch wire slot.

Additionally, when the bracket 10 is in the conformation illustrated in FIG. 3C, the curved hinge-guiding surface 26 of the cam structure 22 is in contact with the inside surface of the elongate film hinge 20. This contact between curved surface 26 and the elongate film hinge 20 distributes forces associated with closing the ligation cover 14 (i.e., while bending the hinge) gradually along the entire contact length between the curved surface 26 and the elongate film hinge 20 as the cover 14 is progressively closed. This results in the elongate film hinge 20 bending along its entire length, or at least a substantial portion of its entire length, as the cover 14 is closed, rather than bending at a single point or line. This characteristic allows the elongate film hinge 20 to bend without kinking, thereby decreasing the likelihood of fatigue and unwanted breakage. Because the elongate film hinge 20 bends gradually along its entire length, rather than abruptly at a distinct localized bending angle, the film hinge 20 can be significantly thicker than film hinges that bend at a discrete localized bending angle. The combination of these characteristics result in a much stronger and more durable hinge that resists breakage when subjected to shearing or bending forces.

Also seen in FIG. 3C, the end of the ligation cover 14 containing the locking tongue 30 begins to make contact with the bracket base 12. As the ligation cover 14 is pushed further closed, the portion of the cover in contact with the base 12 slides along the upper side of the bracket base 12, which causes the ligation cover 14 to flex outwardly so that the locking tongue 30 can pass over the nose 29 of the bracket base 12 and into the angled keyway 28.

Further closing of the ligation cover 14 relative to the bracket base 12 causes the locking tongue 30 to be inserted within the angled keyway 28 (as shown in FIG. 3D). In the conformation depicted in FIG. 3D, the orthodontic bracket 10, more particularly the ligation cover 14, is locked in the closed, ligating position relative to the arch wire slot 16. Because the ligation cover 14 is flexible, it exerts a spring-like action that causes it to resume its original shape. As a result, the locking tongue 30 is pulled by the ligation cover 14 up into the angled keyway 28. In order to open the ligation cover 14, the locking tongue 30 must be physically pulled out of angled keyway 28 and over the nose 29 of the bracket base 12. Past that point, the ligation cover 14 will spontaneously open due to the spring-like action of the cam structure 22.

When there is no arch wire within arch wire slot 16, or when the arch wire 18 is fully seated within the arch wire slot 16 (FIG. 3D), the locking tongue 30 will typically only be inserted part way up the angled keyway 28 in the embodiment depicted in FIGS. 3A–3E. However, in the event that the arch wire 18 is not fully seated within the arch wire slot 16 so that it bears upward against the ligation cover 14 (e.g., against bearing protrusion 32) with sufficient force to cause the ligation cover 14 to bulge upwardly relative to the bracket base 12, the locking tongue 30 will be pulled even more deeply into the angled keyway 28. This has the effect of further tightening the locking mechanism. FIG. 3E shows the locking tongue 30 being pulled more deeply into the angled keyway 28 as a result of the arch wire 18 bearing upwardly against the ligation cover 14.

Accordingly, the interaction of the locking tongue 30 and the angled keyway 28 serve to provide a more secure locking mechanism that prevents inadvertent unlocking and opening of the ligation cover 14 in the event that an arch wire bears upwardly against the ligation cover 14 with enough force to cause it to bulge away from the bracket base. Thus, unlike other latch mechanisms in which an arch wire bearing upwardly against the ligation cover might cause the cover to inadvertently release, the preferred locking mechanism depicted in FIGS. 3A–3E causes the ligation cover 14 to be locked more securely with the bracket base 12 when the arch wire 18 exerts upward pressure relative to the ligation cover 14.

Figure 4A:
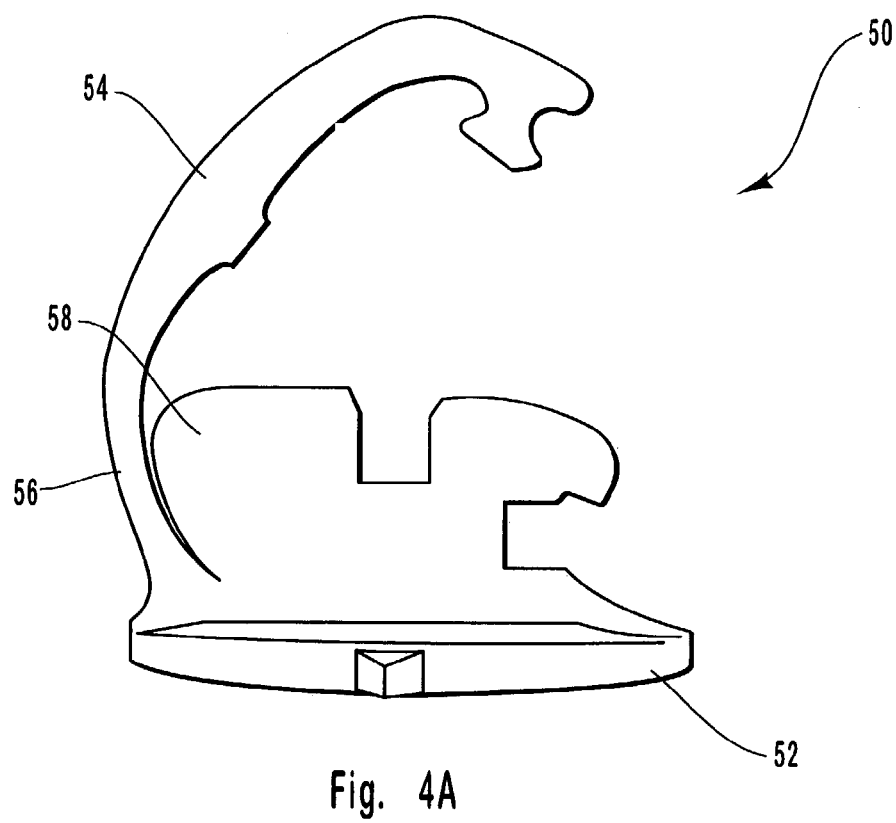
FIGS. 4A and 4B depict an exemplary orthodontic bracket according to the invention that includes a bracket base having a rounded surface that helps guide the elongate film hinge to bend over substantially its entire length.
Figure 4B:
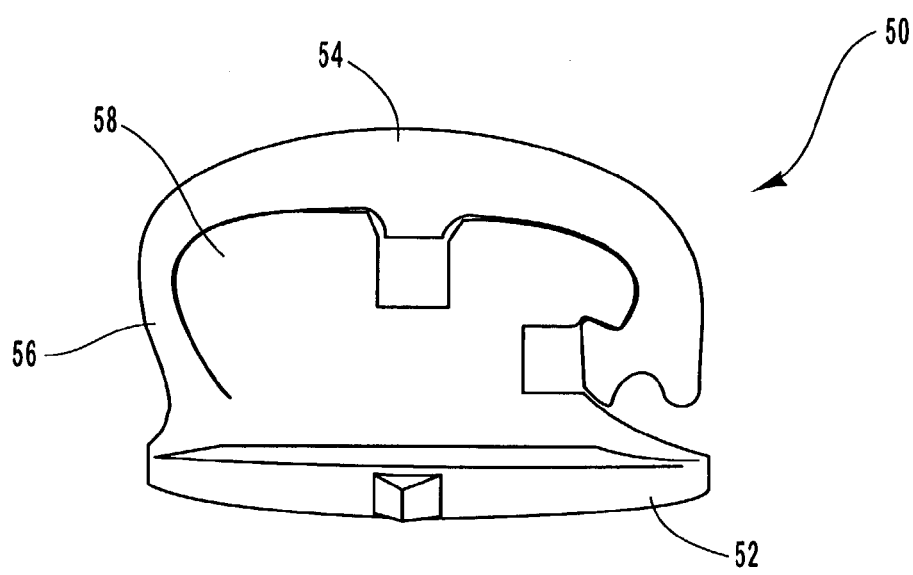

FIGS. 4A and 4B depict an alternative embodiment of an orthodontic bracket 50 according to the invention that does not include a cam structure. Instead, the orthodontic bracket 50 depicted in FIGS. 4A and 4B includes a bracket base 52 and a ligation cover 54 attached to the bracket base 52 by means of an elongate film hinge 56. The bracket base 52 further includes a curved end 58 that acts as a hinge guide in order to cause the elongate film hinge 56 to bend gradually over substantially its entire length. In this way, the curved end 58 of the bracket base 52 acts in similar manner to the curved hinge-guiding surface 24 of the cam structure 22 of the orthodontic bracket 10 depicted in FIGS. 1–3. Thus, as the ligation cover 54 is moved from an open, non-ligating position (FIG. 4A) to a closed, ligating position (FIG. 4B), the elongate film hinge 56 at least partially abuts the curved end 58. The abutment between the elongate film hinge 56 and the curved end 58 causes the elongate film hinge 56 to bend gradually around the curved end 58 so as to better distribute the bending forces and bending angles along substantially the entire length of the elongate film hinge 56.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket comprising:
   a bracket base;
   at least one arch wire slot in the bracket base slot adapted to receive an arch wire therein;
   a ligation cover hingedly connected to the bracket base and selectively rotatable relative to the bracket base between an open, non-ligating position relative to the arch wire slot and a closed, ligating position relative to the arch wire slot;
   an elongate film hinge attached at one end to the bracket base and at an opposite end to the ligation cover so as to hingedly connect the ligation cover to the bracket base, and wherein the elongate film hinge biases the ligation cover toward the open, non-ligating position; and
   a hinge guide structure disposed on the ligation cover or bracket base, the hinge guide structure providing a curved surface around which the elongate film hinge bends when the ligation cover is selectively rotated relative to the bracket base so that the film hinge bends over substantially its entire length.

2. An orthodontic bracket as recited in claim 1, wherein the hinge guide structure comprises a curved surface of the bracket base adjacent to the elongate film hinge.

3. An orthodontic bracket as recited in claim 1, wherein the hinge guide structure comprises a curved surface, proximal to the film hinge, of a cam structure that is attached to inner surface of the ligation cover and that extends toward the bracket base.

4. An orthodontic bracket as recited in claim 3, wherein the curved surface interacts with the elongate film hinge so as to distribute bending forces along substantially the entire length of the elongated film hinge when the ligation cover is selectively rotated relative to the bracket base.

5. An orthodontic bracket as recited in claim 3, wherein the cam structure comprises a camming surface, distal to the film hinge, that interacts with the bracket base so as to bias the ligation cover toward the open, non-ligating position.

6. An orthodontic bracket as recited in claim 3, wherein the camming surface of the cam structure is at least partially curved.

7. An orthodontic bracket as recited in claim 3, wherein the cam structure fits within and substantially fills a void space between the bracket base and the elongate film hinge when the ligation cover is in the closed, ligating position.

8. An orthodontic bracket as recited in claim 3, wherein the bracket base, ligation cover, film hinge, and cam structure are integrally formed together as a single piece of plastic.

9. An orthodontic bracket as recited in claim 8, wherein the orthodontic bracket is formed by injection molding.

10. An orthodontic bracket as recited in claim 1, wherein the elongate film hinge has a cross-sectional thickness tat is less than the cross-sectional thicknesses of the ligation cover and bracket base where the ligation cover and bracket base are attached to the elongate film hinge.

11. An orthodontic bracket as recited in claim 1, further comprising a latch mechanism that selectively locks and unlocks the ligation cover in the closed, ligating position.

12. An orthodontic bracket as recited in claim 11, wherein the latch mechanism comprises an angled keyway within a side of the bracket base distal to the film hinge and a locking tongue extending from an end of the ligation distal to the film hinge, the locking tongue being configured so as to selectively fit within the angled keyway and lock the ligation cover to the bracket base in the closed, ligating position.

13. An orthodontic bracket as recited in claim 1, the ligation covering including a bearing protrusion that extends toward the arch wire slot when the ligation cover is in the closed, ligating position.

14. An orthodontic bracket as recited in claim 1, wherein the elongate film hinge has a thickness in a range of about 0.1 mm to about 0.4 mm.

15. An orthodontic bracket as recited in claim 1, wherein the elongate film hinge has a thickness in a range of about 0.15 mm to about 0.3 mm.

16. An orthodontic bracket as recited in claim 1, wherein the elongate film hinge has a thickness in a range of about 0.2 mm to about 0.26mm.

17. An orthodontic bracket comprising:
a bracket base;
at least one arch wire slot in the bracket base slot adapted to receive an arch wire therein;
a ligation cover hingedly connected to the bracket base and selectively rotatable relative to the bracket base between an open, non-litigating position relative to the arch wire slot and a closed, ligating position relative to the arch wire slot;
an elongate film hinge attached at one end to the bracket base and at an opposite end to the ligation cover so as to hingedly connect the ligation cover to the bracket base; and
a cam structure that is attached to an inner surface of the ligation cover and that extends toward the bracket base, the cam structure comprising a camming surface that interacts with the bracket base so as to bias the ligation cover toward the open, non-ligating position.

18. An orthodontic bracket as recited in claim 17, wherein the camming surface of the cam structure is at least partially curved.

19. An orthodontic bracket as recited in claim 17, wherein the cam structure further comprises a curved surface, proximal to the film hinge and opposite the camming structure, round which the elongate film hinge bends so that the film hinge bends over substantially its entire length when the ligation cover is selectively rotated relative to the bracket base.

20. An orthodontic bracket as recited in claim 19, wherein the curved surface interacts with the elongate film hinge so as to distribute bending forces along substantially the entire length of the elongated film hinge when the ligation cover is selectively rotated relative to the bracket base.

21. An orthodontic bracket as recited in claim 17, wherein the bracket base, ligation cover, film hinge, and cam structure are integrally formed together as a single piece of plastic.

22. An orthodontic bracket comprising:
a bracket base;
at least one arch wire slot in the bracket base slot adapted to receive an arch wire therein;
a litigation cover hingedly connected to the bracket base and selectively rotatable relative to the bracket base between an open, non-litigating position relative to the arch wire slot and a closed, litigating position relative to the arch wire slot;
an elongated film hinge attached at one end of the bracket base and at an opposite end to the ligation cover so as to hingedly connect the litigation cover to the bracket base; and
a cam structure that is attached to an inner surface of the ligation cover and that extends toward the bracket base, the cam structure comprising:
a camming surface that is at least partially curved and that interacts with the bracket base so as to bias the ligation cover toward the open, non-ligating position; and
a curved surface, proximal to the film hinge and opposite the camming structure, around which the elongate film hinge bends so that the film length when hinge bends, and bending forces are distributed, over substantially its entire length when the ligation cover is selectively rotated relative to the bracket base.

23. An orthodontic bracket as recited in claim 22, wherein the bracket base, ligation cover, film hinge, and cam structure are integrally formed together as a single piece of plastic.

* * * * *

UNITED STATES PATENT AND TRADEMARK OFFICE
CERTIFICATE OF CORRECTION

PATENT NO. : 6,960,080 B2 Page 1 of 1
APPLICATION NO. : 10/379331
DATED : November 1, 2005
INVENTOR(S) : Abels et al.

It is certified that error appears in the above-identified patent and that said Letters Patent is hereby corrected as shown below:

Column 9
Line 2, before "inner surface", please insert --an--
Line 27, after "thickness", change "tat" to --that--
Line 53, after "to about", change "0.26mm" to --0.26 mm--

Column 10
Line 16, before "which the" change "round" to --around--
Line 38, after "one end" change "of" to --to--
Line 51, after "that the film" remove "length when"

Signed and Sealed this

Fifth Day of December, 2006

JON W. DUDAS
*Director of the United States Patent and Trademark Office*